United States Patent
Choi et al.

(10) Patent No.: US 11,447,559 B2
(45) Date of Patent: Sep. 20, 2022

(54) ANTI-BCMA ANTIBODY HAVING HIGH AFFINITY FOR BCMA AND PHARMACEUTICAL COMPOSITION FOR TREATMENT OF CANCER, COMPRISING SAME

(71) Applicants: MOGAM INSTITUTE FOR BIOMEDICAL RESEARCH, Yongin-si (KR); GREEN CROSS CORPORATION, Yongin-si (KR); DANA-FARBER CANCER INSTITUTE, INC., Boston, MA (US)

(72) Inventors: Hye-Ji Choi, Yongin-si (KR); Jae-Chan Park, Yongin-si (KR); Hyung-Kwon Lim, Yongin-si (KR)

(73) Assignees: MOGAM INSTITUTE FOR BIOMEDICAL RESEARCH, Yongin-si (KR); GREEN CROSS CORPORATION, Yongin-si (KR); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/649,225

(22) PCT Filed: Sep. 21, 2018

(86) PCT No.: PCT/KR2018/011318
§ 371 (c)(1),
(2) Date: Mar. 20, 2020

(87) PCT Pub. No.: WO2019/066435
PCT Pub. Date: Apr. 4, 2019

(65) Prior Publication Data
US 2020/0299395 A1    Sep. 24, 2020

(30) Foreign Application Priority Data

Sep. 29, 2017  (KR) .......................... 10-2017-0127990

(51) Int. Cl.
| | |
|---|---|
| C07K 16/28 | (2006.01) |
| A61K 39/395 | (2006.01) |
| C12N 15/63 | (2006.01) |
| A61K 39/00 | (2006.01) |

(52) U.S. Cl.
CPC .......... *C07K 16/2878* (2013.01); *C12N 15/63* (2013.01); *A61K 2039/505* (2013.01); *C07K 2317/24* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| | | |
|---|---|---|
| 2015/0284467 A1 | 10/2015 | Lipp et al. |
| 2016/0297885 A1 | 10/2016 | Kuo et al. |

FOREIGN PATENT DOCUMENTS

| | | |
|---|---|---|
| KR | 10-2014-0031905 A | 3/2014 |
| KR | 10-2015-0032337 A | 3/2015 |
| KR | 10-1589785 B1 | 1/2016 |
| WO | 2014/068076 A2 | 5/2014 |
| WO | 2017/025038 A1 | 2/2017 |

OTHER PUBLICATIONS

Written Opinion of the International Searching Authority, PCT/KR2018/011318, English Translation, dated Jan. 31, 2020, pp. 1-8; Anti-BCMA Antibody Having High Affinity For BCMA and Pharmaceutical Composition For Treatment of Cancer, Comprising Same. (Year: 2020).*
D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018.00395. (Year: 2018).*
Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14:2784-2794 (1995). (Year: 1995).*
International Search Report for PCT/KR2018/011318, dated Apr. 17, 2019.

* cited by examiner

*Primary Examiner* — Phillip Gambel
(74) *Attorney, Agent, or Firm* — Sughrue Mion, PLLC

(57) ABSTRACT

Provided according to an embodiment of the present invention is an antibody that binds specifically to B-cell maturation antigen (BCMA) and comprises a heavy chain variable domain (VH domain) composed of a sequence having a homology of 80% or higher with any one of the amino acid sequences of SEQ ID NOS: 1 to 20, or a fragment thereof.

27 Claims, 3 Drawing Sheets
Specification includes a Sequence Listing.

[Fig. 1]
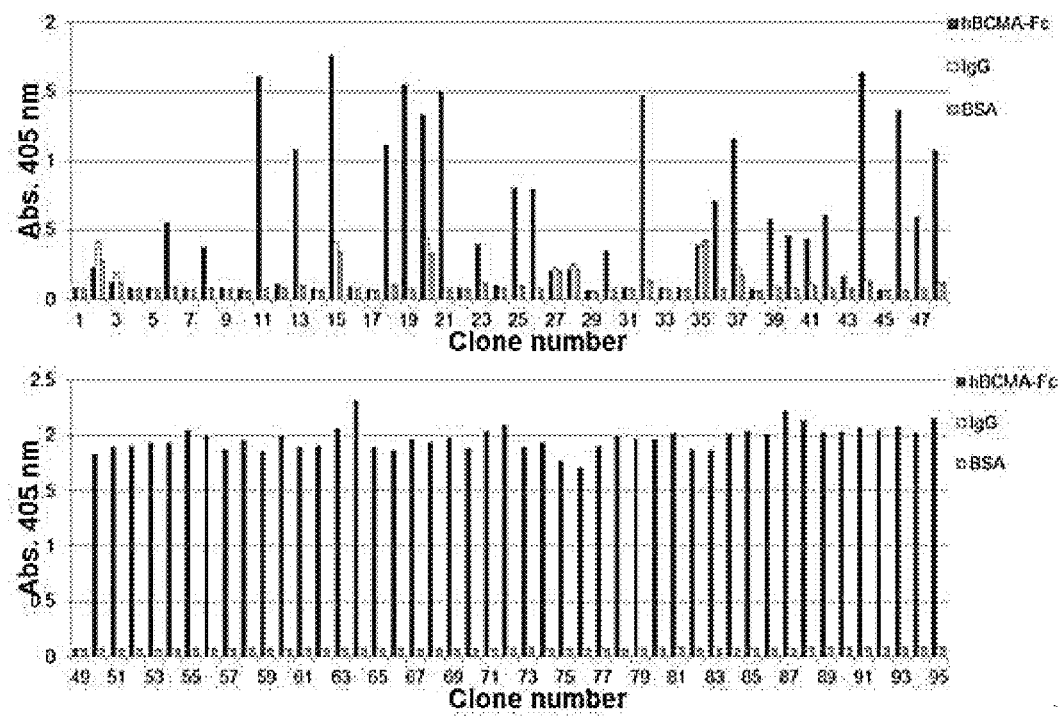
[Fig. 2]
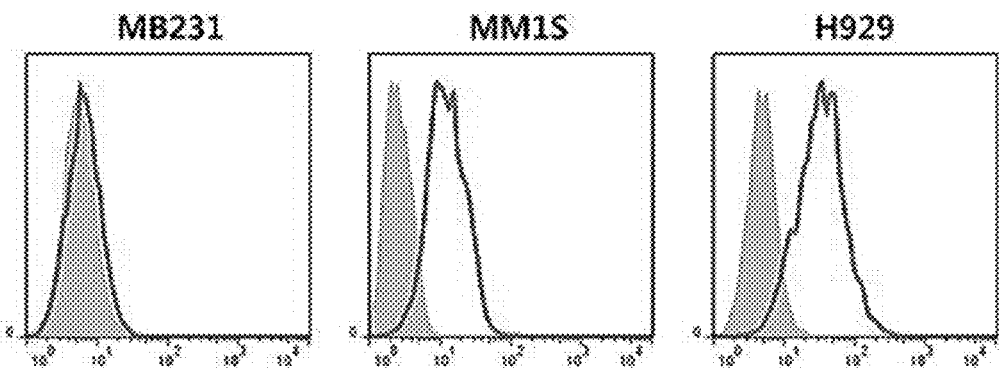

[Fig. 3]
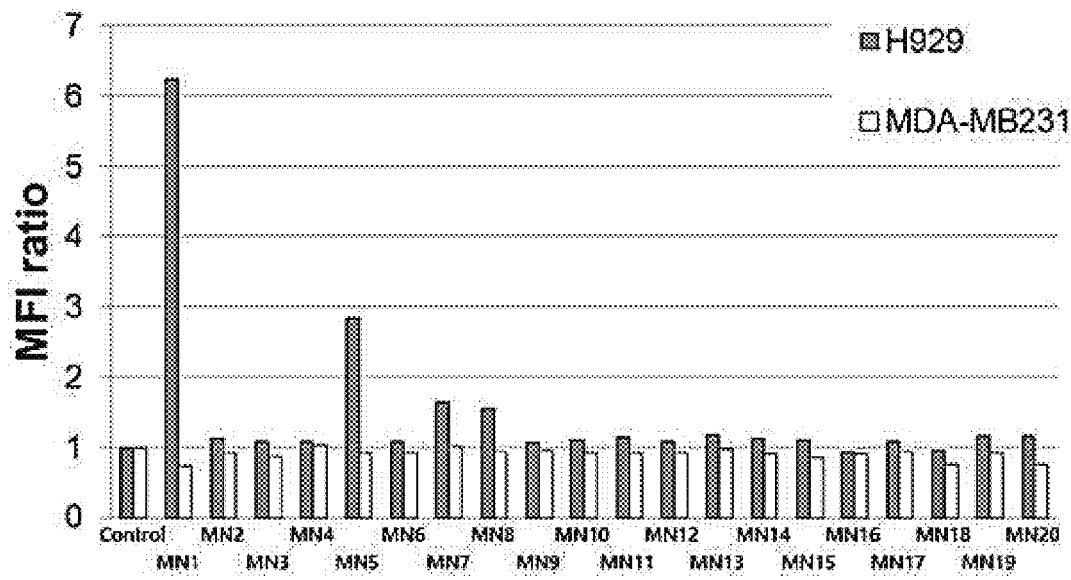
[Fig. 4]
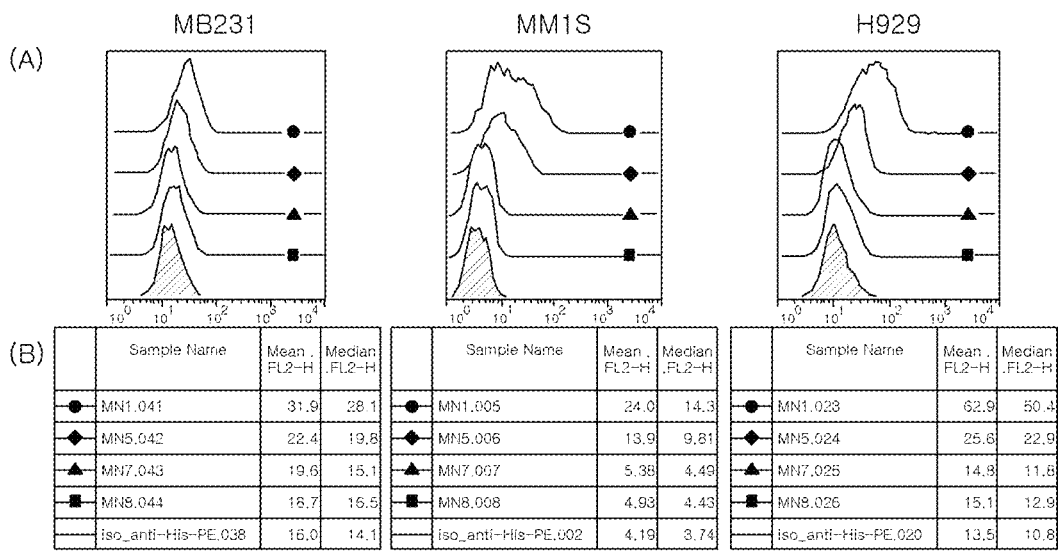

[Fig. 5]
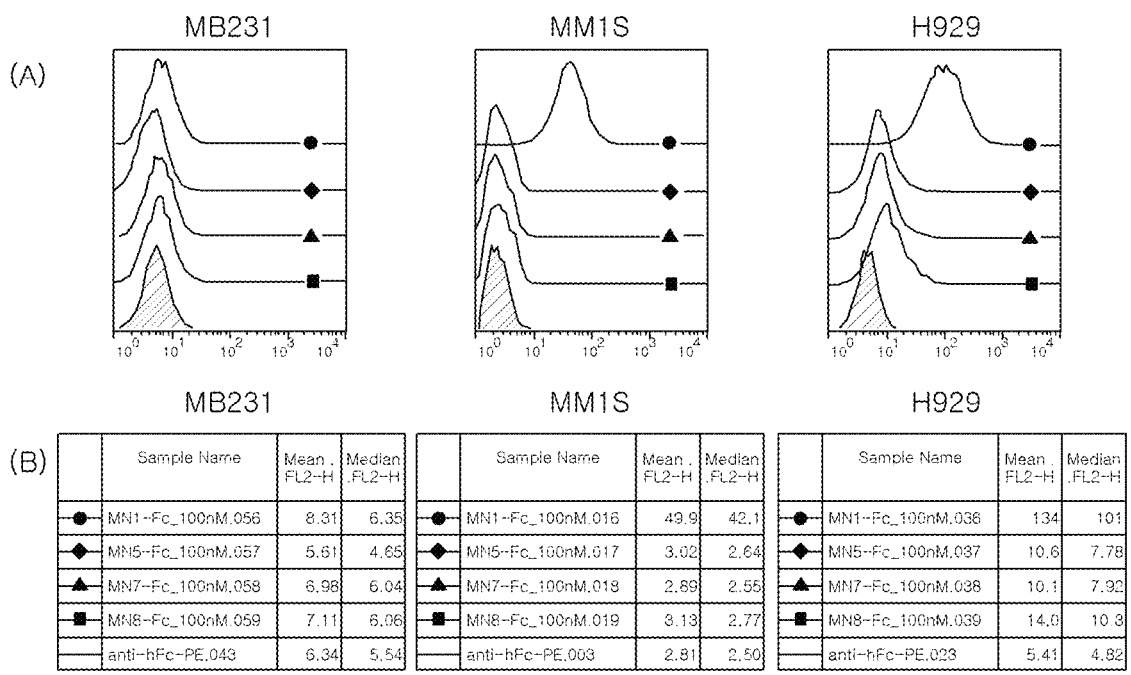

ANTI-BCMA ANTIBODY HAVING HIGH AFFINITY FOR BCMA AND PHARMACEUTICAL COMPOSITION FOR TREATMENT OF CANCER, COMPRISING SAME

CROSS REFERENCE TO RELATED APPLICATIONS

This Application is a National Stage of International Application No. PCT/KR2018/011318 filed Sep. 21, 2018, claiming priority based on Korean Patent Application No. 10-2017-0127990 filed Sep. 29, 2017.

TECHNICAL FIELD

The present invention relates to an anti-BCMA antibody having high affinity to BCMA and a pharmaceutical composition for treating cancer comprising the same.

BACKGROUND ART

B-cell maturation antigen (BCMA), also known as CD269 or tumor necrosis factor receptor superfamily member 17 (TNFRSF17), is expressed at the highest level in terminally differentiated B cells, and functions to maintain long-term humoral immunity by mediating survival of plasma cells.

BCMA is a protein that is not expressed in normal human organs except for plasma cells. Recently, studies have shown that overexpression of BCMA is observed in multiple myeloma (MM).

Multiple myeloma is a type of blood cancer caused by abnormal differentiation and proliferation of plasma cells, which produces tumors and makes bones melt, thereby causing pain. In addition, multiple myeloma invades the bone marrow and decreases levels of white blood cells, red blood cells, and platelets, thereby also increasing the risk of anemia, infection, and bleeding. Furthermore, myeloma cells may produce M protein that is an abnormal immune protein, and this protein may lead to increased blood viscosity, thereby causing blood hyperviscosity syndrome or damaging the kidneys.

Despite such high dangers of multiple myeloma, there is no development of a therapeutic agent that can fundamentally cure the same.

DISCLOSURE OF INVENTION

Technical Problem

The present invention has been made to solve the above-described problems of the prior art, and an object of the present invention is to provide an antibody having high binding affinity to BCMA and a pharmaceutical composition with excellent cancer treatment efficacy using the same.

However, the problem to be solved by the present invention is not limited to the above-mentioned problems, and other problems which are not mentioned will be clearly understood by those skilled in the art from the following description.

Solution to Problem

In order to achieve the above object, the present invention provides an antibody or a fragment thereof, which specifically binds to B-cell maturation antigen (BCMA), comprising a heavy chain variable domain (VH domain) that consists of a sequence having at least 80% homology with the amino acid sequence of any one of SEQ ID NOs: 1 to 20.

In addition, the present invention provides an antibody or a fragment thereof, which specifically binds to BCMA, comprising VH-CDR1 consisting of the amino acid sequence of SEQ ID NO: 21, 24, 27, or 45; VH-CDR2 consisting of the amino acid sequence of SEQ ID NO: 22, 25, 28, or 46; and VH-CDR3 consisting of the amino acid sequence of SEQ ID NO: 23, 26, 29, 30, 31, 32, 33, 34, 35, 36, 37, 38, 39, 40, 41, 42, 43, 44, 47, or 48.

In addition, the present invention provides a polynucleotide that encodes the heavy chain variable domain (VH domain) of the antibody.

In addition, the present invention provides an expression vector comprising the polynucleotide.

In addition, the present invention provides a host cell transformed with the expression vector.

In addition, the present invention provides a method for producing an antibody that specifically binds to BCMA, comprising culturing the host cell.

In addition, the present invention provides a pharmaceutical composition for preventing or treating cancer, comprising the antibody or a fragment thereof.

In addition, the present invention provides a method for preventing or treating cancer, comprising administering the pharmaceutical composition to a subject.

Advantageous Effects of Invention

Due to high affinity and specificity to BCMA, an antibody of the present invention can be effectively used for prevention or treatment of cancer.

It is to be understood that the effect of the present invention is not limited to the above-described effects, and includes any effects deducible from the features of the invention described in the detailed description or the claims of the present invention.

BRIEF DESCRIPTION OF DRAWINGS

FIG. 1 illustrates results obtained by measuring the OD value of clone candidates using ELISA.

FIG. 2 illustrates results obtained by analyzing the BCMA expression level in multiple myeloma cell lines.

FIG. 3 illustrates the relative binding capacity of anti-BCMA antibodies to BCMA-expressing tumor cell lines.

FIG. 4 illustrates results obtained by analyzing the binding affinity to BCMA-expressing cell lines of anti-BCMA antibodies (VH domains) according to an embodiment of the present invention.

FIG. 5 illustrates results obtained by analyzing the binding affinity to BCMA-expressing cell lines of anti-BCMA antibodies (VH-Fc proteins) according to an embodiment of the present invention.

BEST MODE FOR CARRYING OUT THE INVENTION

Hereinafter, embodiments will be described in detail with reference to the accompanying drawings.

Various modifications may be made to the embodiments as described below. It is to be understood that the embodiments as described below are not intended to limit the embodied forms of the present invention and the present invention encompasses all modifications, equivalents, and substitutes thereto.

The terminology used in the embodiments is merely given to describe a particular embodiment and is not intended to limit the embodiment. As used herein, the meaning of "a,", "an," and "the" includes plural reference unless the context clearly dictates otherwise. It is to be understood that in the present specification, the terms such as "comprise" or "have" specify the presence of features, integers, steps, operations, elements, or components, or combinations thereof as stated herein, and do not preclude the presence or addition of one or more other features, integers, steps, operations, elements, or components, or combinations thereof.

Unless defined otherwise, all terms used herein, including technical or scientific terms, have the same meaning as commonly understood by one of ordinary skill in the art to which the embodiment belongs. Terms such as those defined in the commonly used dictionaries should be interpreted as having meanings consistent with the meanings in the context of the related technology, and will not be interpreted in an idealized or overly formal sense unless expressly defined so in this application.

In addition, in describing the embodiments, when it is determined that a specific description of the related known technology may unnecessarily obscure the gist of the embodiment, the specific description will be omitted.

As used herein, the term "BCMA" may mean a concept that collectively refers to BCMA itself, and any variant, isotype, and paralog thereof, which are present in an animal and preferably in the human body.

As used herein, the term "human BCMA" refers to a human-derived BCMA, and may preferably have, but is not limited to, the amino acid sequence of Genbank Accession No. AB052772.1.

As used herein, the term "antibody" refers to an immunoglobulin (Ig) molecule immunologically reactive with a particular antigen, that is, a protein molecule that acts as a receptor that specifically recognizes an antigen, and may mean a concept that encompasses both whole antibodies and antibody fragments.

In an aspect of the present invention, there is provided an antibody or a fragment thereof, which specifically binds to B-cell maturation antigen (BCMA), comprising a heavy chain variable domain (VH domain) that consists of a sequence having at least 80% homology with the amino acid sequence of any one of SEQ ID NOs: 1 to 20. The heavy chain variable domain having the amino acid sequence of any one of SEQ ID NOs: 1 to 20 can specifically bind to BCMA, and in particular, the amino acid sequence of SEQ ID NO: 1, 5, 7, or 8 can bind with higher affinity to BCMA.

The heavy chain variable domain may consist of an amino acid sequence having at least 80%, preferably at least 90%, more preferably at least 95%, and most preferably at least 99% homology with the amino acid sequence of any one of SEQ ID NOs: 1 to 20.

In the heavy chain variable domain, some amino acids may be substituted, inserted, and/or deleted as long as properties consistent with the object of the present invention, such as affinity and specificity to BCMA, are maintained. For example, conservative substitutions of amino acids may occur in the heavy chain variable domain. The conservative substitution means a substitution of an original amino acid with another amino acid residue having a similar property.

For example, lysine, arginine, and histidine have similar properties in that they have a basic side chain, and aspartic acid and glutamic acid have similar properties in that they have an acidic side chain. In addition, glycine, asparagine, glutamine, serine, threonine, tyrosine, cysteine, and tryptophan have similar properties in that they have a non-charged polar side chain; alanine, valine, leucine, threonine, isoleucine, proline, phenylalanine, and methionine have similar properties in that they have a nonpolar side chain; and tyrosine, phenylalanine, tryptophan, and histidine have similar properties in that they have an aromatic side chain.

Therefore, it is apparent to those skilled in the art that the amino acid substitutions within the group of the amino acids having similar properties as described above will not cause any significant change in the properties. For this reason, antibodies that have undergone variation caused by a conservative substitution within the variable domain are also included in the scope of the present invention as long as such antibodies maintain properties of the antibody of the present invention.

The heavy chain variable domain of the antibody may consist of complementarity determining regions (CDRs) and framework regions (FRs). The CDRs confer binding specificity to a particular antigen, and a set of the CDRs (CDR1, CDR2 and CDR3) provides a binding site for the antigen.

Thus, the present invention provides an antibody or a fragment thereof, which specifically binds to BCMA, comprising VH-CDR1 that consists of the amino acid sequence of SEQ ID NO: 21, 24, 27, or 45; VH-CDR2 that consists of the amino acid sequence of SEQ ID NO: 22, 25, 28, or 46; and VH-CDR3 that consists of the amino acid sequence of SEQ ID NO: 23, 26, 29, 30, 31, 32, 33, 34, 35, 36, 37, 38, 39, 40, 41, 42, 43, 44, 47, or 48. The "VH-CDR" refers to a CDR of a heavy chain variable domain (VH domain).

In addition, when the antibody contains VH-CDR1 that consists of the amino acid sequence of SEQ ID NO: 21 or 27; VH-CDR2 that consists of the amino acid sequence of SEQ ID NO: 22 or 28; and VH-CDR3 that consists of the amino acid sequence of SEQ ID NO: 23, 31, 33, or 34, such an antibody may have higher binding affinity to BCMA.

Meanwhile, the antibody may be a humanized antibody that specifically binds to human BCMA. As used herein, the term "humanized antibody" refers to a chimeric antibody that contains a minimal sequence derived from an immunoglobulin of a non-human antibody, such as a mouse antibody, and may mean an antibody in which all parts except the sequence corresponding to a hypervariable region are substituted with sequences of a human antibody.

In addition, the term "hypervariable region (HVR)" refers to a region of a variable domain which exhibits hypervariability or forms a structurally defined loop in the sequence of an antibody. Among definitions identifying the same, the complementarity determining region (CDR) definition according to Kabat is most commonly used to classify regions based on sequence variability.

For the antibody, an antibody fragment thereof may also be used as long as the antibody fragment maintains the antibody's function. The antibody or antibody fragment may include, but is not limited to, single-chain antibodies, diabodies, triabodies, tetrabodies, Fab fragments, F(ab')2 fragments, Fd's, scFv's, domain antibodies, minibodies, scAb's, IgD antibodies, IgE antibodies, IgM antibodies, IgG1 antibodies, IgG2 antibodies, IgG3 antibodies, IgG4 antibodies, derivatives of antibody's constant regions, artificial antibodies based on protein scaffolds, and the like, which maintain a binding function to BCMA, and may preferably be a single-domain antibody (sdAb) obtained by binding of a heavy chain variable region (VH region) with an Fc region.

Specifically, the fragment of the antibody may be a single-domain antibody (sdAb). As used herein, the term "single-domain antibody" is an antibody fragment consisting of a single monomeric variable antibody domain and may selectively bind to a particular antigen. The single-domain antibody is a peptide chain of about 110 amino acids which contains one heavy chain variable domain. This single-domain antibody has an affinity similar to that of the whole antibody, but is more heat-resistant and stable towards detergents, high concentrations of urea, and the like.

The single-domain antibody may be obtained by immunization of camels, llamas, alpacas, sharks, and the like with a desired antigen, followed by isolation of mRNA encoding a heavy chain antibody. Subsequently, through reverse transcription or polymerase chain reaction, it is possible to prepare a gene library of single-domain antibodies containing millions of clones. In addition, clones that bind to a particular antigen can be identified using a technique such as phage display and ribosome display.

In an embodiment of the present invention, the phage display technique was used to select single-domain antibodies that specifically bind to BCMA.

Meanwhile, the antibody may also be used in the form of an antibody-drug conjugate (ADC) obtained by attaching the antibody to an anticancer drug having tumor-cell proliferation inhibition efficacy. As used herein, the term "anticancer" includes "prevention" and "treatment" effects on cancer, and the "prevention" means any act of inhibiting or delaying cancer. In addition, the "treatment" means any act of ameliorating or beneficially altering symptoms of cancer.

The drug that can be used in the antibody-drug conjugate includes any compound having a cytotoxic or cytostatic effect, and a part or functional group of the compound. Examples of the drug include microtubulin structure formation inhibitors, meiosis inhibitors, RNA polymerase inhibitors, topoisomerase inhibitors, DNA intercalators, DNA alkylators, ribosomal inhibitors, miRNAs, shRNAs, siRNAs, radioisotopes, and toxins, among which at least one compound may be used.

The drug may include, but is not limited to, maytansinoid, auristatin, dolastatin, trichothecene, CC1065 (NSC 298223), calicheamicin, taxane, anthracycline, methotrexate, adriamycin, vindesine, vinca alkaloids (vincristine, vinblastine, etoposide), doxorubicin, melphalan, mitomycin C, chlorambucil, daunorubicin, daunomycin, etoposide, teniposide, carminomycin, aminopterin, dactinomycin, mitomycins, bleomycins, esperamicins, other enediyne antibiotics, 5-fluorouracil, other nitrogen mustards and stereoisomers, isosteres, homologs, or derivatives thereof, cis-platinum and cis-platinum homologs, other intercalator enzymes and fragments thereof, for example, nucleases, antibiotics, toxins (enzymatically active toxins or small molecule toxins of bacterial, fungal, plant, or animal origin), and various anti-tumor or anticancer agents such as cisplatin, CPT-11, paclitaxel, and docetaxel.

In addition, the radioisotope (radionuclide) includes 3H, 14C, 32P, 35S, 36Cl, 51Cr, 57Co, 58Co, 59Fe, 90Y, 125I, 131I, 186Re, and the like. MicroRNAs (miRNAs), siRNAs, shRNAs, and the like may also be used which can inhibit expression of certain oncogenes.

Attachment of the anti-BCMA antibody to a drug is preferably achieved by conjugation using a functional group such as a thiol group of an amino acid residue such as lysine or cysteine in the antibody. If necessary, it is also possible to perform conjugation in a linker-mediated form which is commonly used. A maleimide- or iodine acetamide-based linker may also be used.

When a drug is conjugated to the antibody or a fragment thereof, the drug may be conjugated to the C-terminal site, which is opposite to an antigen binding site, from the viewpoint of decreasing an effect on the antibody or fragment's binding capacity and specificity to BCMA. When the whole antibody, rather than a fragment thereof, is used, the drug may be conjugated to an Fc region.

In addition, the antibody may also be used as a chimeric antigen receptor (CAR)-based therapeutic agent containing the same. Examples of such a therapeutic agent preferably include, but are not limited to, chimeric antigen receptor T cell (CAR-T cell) or chimeric antigen receptor natural killer cell (CAR-NK cell) therapeutics.

The antibody may also be used in the form of a bispecific antibody containing an anti-BCMA antibody. The bispecific antibody is an antibody that has capacity of binding to two antigens at the same time, and may typically exist in a form in which heavy and light chain pairs that bind to different antigens are linked to each other.

In addition, the bispecific antibody is available in a form such as a bispecific single-chain antibody where single-chain antibody fragments (scFv's), in which VL and VH are linked to each other via a short linker peptide, are connected in the form of scFv1-scFv2(-Fc), a single-domain antibody (sdAb)-based dual antibody using VH, and a bispecific antibody generated using BiTE technology (see www.micromet.de) from Micromet, Germany.

The bispecific antibody may exist in a form in which the anti-BCMA antibody is bound to an antibody or a fragment thereof having binding capacity to an immunopotent cell-specific target molecule. The immunopotent cell-specific target molecule may preferably be selected from, but is not limited to, TCR/CD3, CD16 (FcγRIIIa), CD44, CD56, CD69, CD64 (FcγRI), CD89, and CD11b/CD18 (CR3).

In another aspect of the present invention, there are provided a polynucleotide that encodes a heavy chain variable domain (VH domain) of the antibody according to the present invention and an expression vector comprising the same.

The polynucleotide that encodes the heavy chain variable domain of the antibody or antibody fragment (i.e., gene) may be easily derived by those skilled in the art from the amino acid sequence of the anti-BCMA antibody.

As used herein, the term "expression vector" refers to a recombinant vector capable of expressing a target protein in a host cell, and means a gene construct that contains essential regulatory elements operably linked thereto so that an inserted gene is expressed. The gene encoding the anti-BCMA antibody may be inserted into a separate vector or may be used in a form of being inserted into the same vector.

Specifically, the polynucleotide that encodes the amino acid sequence of the anti-BCMA antibody may be used in a form of being inserted into a separate or the same vector, and the polynucleotide that encodes the heavy chain or a variable domain thereof may be used in a form of being inserted into a separate or the same vector.

As used herein, the term "operably linked" means that a nucleic acid expression regulatory sequence and a nucleic acid sequence encoding a desired protein are functionally linked to perform a desired function. Operable linkage with a recombinant vector may be achieved using genetic recombination techniques well known in the art, and site specific DNA cleavage and ligation may be easily achieved using enzymes and the like commonly known in the art.

Expression vectors suitable for production of the anti-BCMA antibody may contain signal sequences for membrane targeting or secretion in addition to expression regulatory elements such as promoters, initiation codons, termination codons, polyadenylation signals, and enhancers. Initiation codons and termination codons are generally considered to be part of a nucleotide sequence encoding an immunogenic target protein. Such codons must be functional in a subject when a gene construct is administered and must be in frame with a coding sequence. In general, promoters may be constitutive or inducible. The promoter may include, but is not limited to, prokaryotic promoters such as lac, tac, T3, and T7, simian virus 40 (SV40) promoters, mouse breast tumor virus (MMTV) promoters, human immunodeficiency virus (HIV) promoters, for example, long terminal repeat (LTR) promoter of HIV, Moloney virus promoters, cytomegalovirus (CMV) promoters, Epstein bar virus (EBV) promoters, Rous sarcoma virus (RSV) promoters, as well as β-actin promoters, human hemoglobin-, human muscle creatine-, human metallothionein-derived eukaryotic promoters, and the like.

The expression vector may further contain a selectable marker that allows for selection of host cells containing the same. The selectable marker is for selecting cells transformed with the vector. For the selectable marker, markers may be used which confer a selectable phenotype, such as drug resistance, auxotrophy, resistance to cytotoxic agents, or expression of surface proteins. In an environment treated with a selective agent, only cells expressing a selection marker survive, which allows for selection of transformed cells. In addition, when the vector is a replicable expression vector, such a vector may contain a replication origin that is a specific nucleic acid sequence from which replication is initiated.

As a recombinant expression vector for insertion of a foreign gene, various forms of vectors such as plasmids, viruses, and cosmids may be used. The type of recombinant vector is not particularly limited as long as the vector functions to express a desired gene and produce a desired protein in various host cells including prokaryotic and/or eukaryotic cells. The vector may preferably be a vector capable of producing a large amount of foreign protein that is in a form similar to its natural state while having a promoter with strong activity and strong expression capacity.

Various expression host/vector combinations may be used to express the anti-BCMA antibody. The expression vector suitable for eukaryotic hosts includes, but is not limited to, expression regulatory sequences derived from SV40, bovine papillomavirus, adenovirus, adeno-associated virus, cytomegalovirus, and retrovirus. The expression vector that may be used in bacterial hosts includes bacterial plasmids obtained from $Escherichia\ coli$, such as pET, pRSET, pBluescript, pGEX2T, pUC vector, colE1, pCR1, pBR322, pMB9, and derivatives thereof; plasmids having a wide host range such as RP4; phage DNAs that may be exemplified by a wide variety of phage lambda derivatives such as λgt10, λgt11, and NM989; and other DNA phages such as M13 and filamentous single-stranded DNA phages. The expression vector useful for yeast cells may include 2-micron plasmids and derivatives thereof. The vector useful for insect cells may be pVL941.

In yet another aspect of the present invention, there is provided a host cell, transformed with the expression vector according to the present invention. The expression vector may be inserted into a host cell to form a transformant. A suitable host cell for the vector may include prokaryotic cells such as $Escherichia\ coli$, $Bacillus\ subtilis$, $Streptomyces$ sp., $Pseudomonas$ sp., $Proteus\ mirabilis$, or $Staphylococcus$ sp. In addition, the host cell may include eukaryotic cells including lower eukaryotic cells from fungi such as $Aspergillus$ sp., yeasts such as $Pichia\ pastoris$, $Saccharomyces\ cerevisiae$, $Schizosaccharomyces$ sp., and $Neurospora$ $crassa$, and other lower eukaryotes, and higher eukaryotic cells such as insect cells. In addition, the host cell may also be derived from plants or mammals. Preferably, the host cell that may be used includes, but is not limited to, monkey kidney cells (COST cells), NSO cells (myeloma cells of mouse origin), SP2/0 cells (myeloma cells of mouse origin), other myeloma cell lines, Chinese hamster ovary (CHO) cells, W138 cells (diploid human cell culture), baby hamster kidney (BHK) cells, MDCK, HuT 78 cells, HEK293 cells, and the like, with CHO cells being preferred.

As used herein, the term "transformation into host cells" is intended to include any method for introducing a nucleic acid into an organism, cell, tissue, or organ and, and such transformation may be performed using a standard technique known in the art selected depending on the type of host cell. Specifically, electroporation, protoplast fusion, calcium phosphate ($CaPO_4$) precipitation, calcium chloride ($CaCl_2$)) precipitation, agitation using silicon carbide fiber, $agrobacterium$-mediated transformation, PEG-, dextran sulfate-, lipofectamine-, or desiccation/inhibition-mediated transformation, or the like may be used. However, the present invention is not limited thereto.

Meanwhile, in still yet another aspect of the present invention, there is provided a method for producing an antibody that specifically binds to BCMA, comprising culturing the host cell. Specifically, the method for producing an antibody may comprise inserting, into a vector, a nucleotide sequence encoding the anti-BCMA antibody, to construct a recombinant vector; transforming a host cell with the recombinant vector and performing culture; and separating and purifying a humanized antibody from the cultured transformant.

The humanized antibodies may be produced in a large amount by culturing the transformant, in which the recombinant vector is expressed, in a nutrient medium, and the medium and culture conditions may be appropriately selected from those known in the art depending on the type of host cell. In culture, conditions such as temperature, pH of a medium, and culture time may be appropriately adjusted to be suitable for cell growth and mass production of a protein.

The recombinantly produced anti-BCMA antibodies as described above may be recovered from a medium or a cell lysate. When the antibody is in a membrane-bound form, such an antibody may be liberated from the membrane using a suitable surfactant solution (for example, Triton-X 100) or by enzymatic cleavage. Cells used for expression of humanized antibodies may be disrupted by various physical and chemical means such as freeze-thaw cycles, sonication, mechanical disruption, or cell lysis agents, and separation and purification may be performed using conventional biochemical separation techniques. The biochemical separation technique that may be used includes, but is not limited to, electrophoresis, centrifugation, gel filtration, precipitation, dialysis, chromatography (ion-exchange chromatography, affinity chromatography, immunoabsorbent chromatography, size exclusion chromatography, or the like), isoelectric focusing, and the like.

In addition, in still yet another aspect of the present invention, there is provided a pharmaceutical composition for preventing or treating cancer, comprising an antibody according to the present invention or a fragment thereof. The type of cancer that can be treated with the pharmaceutical composition may include both solid cancer and blood cancer, preferably may include any cancers in which BCMA is expressed, and more preferably may be multiple myeloma (MM). However, the cancer is not limited thereto.

The pharmaceutical composition may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration.

Preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms.

In addition, the pharmaceutical composition may contain a surfactant that can improve membrane permeability. These surfactants may be derived from steroids or may include cationic lipids such as N-[1-(2,3-dioleoyl)propyl-N,N,N-trimethylammonium chloride (DOTMA), or various compounds such as cholesterol hemisuccinate and phosphatidyl glycerol. However, the surfactant is not limited thereto.

In addition, the present invention provides a method for preventing or treating cancer, comprising administering, to a subject, a pharmaceutical composition according to the present invention. A pharmaceutical composition comprising the anti-BCMA antibody may be administered in a pharmaceutically effective amount to treat cancer cells or metastasis thereof or to inhibit cancer growth. The effective amount may vary depending on various factors such as type of cancer, the patient's age, weight, nature and severity of symptoms, type of current therapy, number of treatments, dosage form, and route of administration, and may be easily determined by experts in the corresponding field.

The pharmaceutical composition may be administered together or sequentially with the above-mentioned pharmacological or physiological components, and may also be administered in combination with additional conventional therapeutic agents, in which case the pharmaceutical composition may be administered sequentially or simultaneously with the conventional therapeutic agents. Such administration may be single or multiple administration. Taking all of the above factors into consideration, it is important to administer an amount that is a minimum amount and allows the maximum effect to be obtained without side effects, and such an amount may be easily determined by those skilled in the art.

As used herein, the term "subject" refers to a mammal, preferably human, suffering from or at risk of a condition or disease that can be alleviated, inhibited, or treated by administration of the pharmaceutical composition.

As used herein, the term "administration" means introducing a predetermined substance into a subject in any suitable manner, and the pharmaceutical composition may be administered via any route as long as the route allows the pharmaceutical composition to reach a target tissue. Such an administration method may include, but is not limited to, intraperitoneal administration, intravenous administration, intramuscular administration, subcutaneous administration, intradermal administration, oral administration, topical administration, intranasal administration, pulmonary administration, or rectal administration. Here, in a case of being orally administered, from the viewpoint that proteins are digested, it may be desirable to formulate a composition for oral use so that an active agent is coated or the composition is protected from digestion in the stomach. In addition, the pharmaceutical composition may be administered by any device such that an active ingredient can migrate to its target cell.

MODE FOR THE INVENTION

Hereinafter, the present invention will be described in more detail by way of examples. The following examples are described for the purpose of illustrating the present invention, and the scope of the present invention is not limited thereto.

Example 1: Preparation of Anti-BCMA Antibody (1) Selection of Anti-Human BCMA sdAb Antibody Using Phage Display A gene recombination technique was used to insert a gene sequence to be expressed into the genome of bacteriophage that is parasitic in *E. coli*, and antibody selection was performed using a phage display technique, by which the inserted gene is expressed, in the form of being fused with one of phage coat proteins, on the phage surface.

At the first panning, 1 ml of $10^{13}$ or higher library stock was allowed to react for 2 hours at 37° C. in a solid phase polystyrene tube (Nunc, 444202) coated with BCMA. At the same time, 10 μl of XLI-Blue electroporation-competent cells (Stratagene) was inoculated in Smith-Baskerville (SB) medium 10 ml/tetracycline 10 μl, and culture was performed until the OD600 value reaches 0.8 to 1.0.

The product obtained by the reaction at 37° C. for 2 hours was washed four times with 5 ml of 0.05% Tween 20/PBS, and the number of washings with 5 ml of 0.05% Tween 20/PBS was increased starting from the second panning point as the number of pannings increases. Then, the resultant was incubated with 1% BSA/0.1 M glycine pH 2.0 at room temperature for 10 minutes, to purify phagemids.

The purified phagemids were transferred to a 50 ml tube and neutralized with 70 μl of 2M Tris. Treatment with 9 ml of XLI-Blue electroporation-competent cells (Stratagene) was performed and 1 ml of the cells was used to treat the washed tube. Infection was allowed to occur at room temperature for 30 minutes. Then, 10 ml of SB, 20 μl of tetracycline, and 10 μl of carbenicillin were added and suspension culture was performed at 37° C. and 220 rpm for 1 hour.

Subsequently, the resultant was subjected to treatment with 1 ml ($10^{11}$ pfu's) of VCS M13 helper phage. Then, suspension culture was performed at 37° C. and 220 rpm for 1 hour, and treatment with 80 ml of SB, 100 μl of kanamycin, and 100 μl of carbenicillin was performed. Then, culture was performed at 37° C. and 220 rpm for 12 hours or longer. The culture was centrifuged at a condition of 3,500 rpm, 4° C., and 10 minutes. Then, the supernatant was transferred to a new tube. 20 ml of 20% PEG/15% NaCl was added thereto and mixed. Then, reaction was allowed to proceed on ice for 30 minutes.

Then, centrifugation was performed at 8,000 rpm, 4° C., and 30 minutes. The supernatant was discarded, and pellets were collected and resuspended with 2 ml of 1% BSA/PBS. Then, centrifugation was performed at 15,000 rpm and 4° C. for 10 minutes. Here, the collected pellets were discarded; and 1 ml of the 2 ml supernatant was stored at −20° C. and the other 1 ml was used in the next panning round.

(2) Obtaining of Individual Clones According to ELISA Method

Single colonies of the finally amplified population of heavy chain variable domain (VH domain) synthesized through the phage display were collected. Then, culture was performed in 1.5 ml of SB/carbenicillin at 37° C. and 220 rpm until the OD600 value reaches about 0.8 to 1.0, and culture was performed with 1 mM IPTG at 30° C. and 200 rpm for 12 hours or longer. The cultures were centrifuged at 5,500 rpm for 5 minutes, and then only each supernatant was added to an ELISA plate coated with BCMA antigen. Reaction was allowed to proceed at room temperature for 2 hours, and then washing was performed four times with PBST (1×PBS, 0.05% Tween 20). HRP/anti-hFab-HRP conjugate diluted to 1/5,000 with 1% BSA/1×PBS was added thereto and reaction was allowed to proceed at room temperature for 1 hour. Then, washing with PBST (1×PBS, 0.05% Tween 20) was performed again four times. A TMB solution was added thereto and reaction was allowed to proceed for 5 to 10 minutes. Next, a TMB stop solution was added thereto. OD values were read using TECAN's Sunrise at a measurement wavelength of 450 nm, and clones having a high OD value were obtained as individual clones.

As can be seen from the results illustrated in FIG. 1, it was possible to obtain a total of 70 clones having a significant OD value. Sequencing was performed on these clones. As a result, it was possible to select 20 clones that specifically bind to human BCMA. The selected clones were designated, respectively, Clone MN1, Clone MN2, Clone MN3, Clone MN4, Clone MN5, Clone MN6, Clone MN7, Clone MN8, Clone MN9, Clone MN10, Clone MN11, Clone MN12, Clone MN13, Clone MN14, Clone MN15, Clone MN16, Clone MN17, Clone MN18, Clone MN19, and Clone MN20.

The variable domain sequence of each clone was identified and is shown in Table 1. The CDR amino acid sequence in the variable domain of each clone was identified and is shown in Table 2 according to Kabat numbering.

TABLE 1

| Clone | Variable domain | Amino acid sequence | SEQ ID NO |
|---|---|---|---|
| MN1 | Heavy chain | EVQLVESGGGLVQPGGSLRLSCAASGFTFTAYDMGWVRQAPGKGPEWVSL ISSDSGDTWYDDSVKGRFTISRDNSKNTLYLQMNSLRAEDTAVYYCARLGA YSTTYDYWGQGTLVTVSS | 1 |
| MN2 | Heavy chain | EVQLVESGGGLVQPGGSLRLSCAASGFTFTNYDMGWVRQAPGKGPEWVSL ISGGSETWYDDSVKGRFTISRDNSKNTLYLQMNSLRAEDTAVYYCAKMETS HTNDTDYWGQGTLVTVSS | 2 |
| MN3 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASFRKT TQETNTWGQGTLVTVSS | 3 |
| MN4 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASMRL PYSNEASHTWGQGTLVTVSS | 4 |
| MN5 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASRED NMTTWGQGTLVTVSS | 5 |
| MN6 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASLRSP SQHHGRWGQGTLVTVSS | 6 |
| MN7 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASPED MYQTWGQGTLVTVSS | 7 |
| MN8 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASPED APSYSRWGQGTLVTVSS | 8 |
| MN9 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASPEDT YQPWGQGTLVTVSS | 9 |
| MN10 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASYLRP RTEAHNTWGQGTLVTVSS | 10 |
| MN11 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASYQSP GADAHNRWGQGTLVTVSS | 11 |
| MN12 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASFRFS TIQMNQWGQGTLVTVSS | 12 |
| MN13 | Heavy chain | EVQLVESGGGLVQPGGSLRLSCAASGFTFSSYAMGWVRQAPGKGPEVVSLI SGSGGSTWYDDSVKGRFTISRDNSKNTLYLQMNSLRAEDTAVYYCASYPH DGNPWGQGTLVTVSS | 13 |

TABLE 1-continued

| Clone | Variable domain | Amino acid sequence | SEQ ID NO |
|---|---|---|---|
| MN14 | Heavy chain | EVQLVESGGGLVQPGGSLRLSCAASGFTFSSYAMGWVRQAPGKGPEVVSLISGSGGSTWYDDSVKGRFTISRDNSKNTLYLQMNSLRAEDTAVYYCASFRPPECQAPGWGQGTLVTVSS | 14 |
| MN15 | Heavy chain | EVQLVESGGGLVQPGGSLRLSCAASGFTFSSYAMGWVRQAPGKGPEVVSLISGSGGSTWYDDSVKGRFTISRDNSKNTLYLQMNSLRAEDTAVYYCASFRRYQSETNTWGQGTLVTVSS | 15 |
| MN16 | Heavy chain | EVQLVESGGGLVQPGGSLRLSCAASGFTFSSYAMGWVRQAPGKGPEVVSLISGSGGSTWYDDSVKGRFTISRDNSKNTLYLQMNSLRAEDTAVYYCASFSTPSSSRHNWGQGTLVTVSS | 16 |
| MN17 | Heavy chain | EVQLVESGGGLVQPGGSLRLSCAASGFTFSSYAMGWVRQAPGKGPEVVSLISGSGGSTWYDDSVKGRFTISRDNSKNTLYLQMNSLRAEDTAVYYCASALAPFKTTLKWGQGTLVTVSS | 17 |
| MN18 | Heavy chain | EVQLVESGGGLVQPGGSLRLSCAASGFTFSSYAMGWVRQAPGKGPEVVSLISGGGSTWYDDSVKGRFTISRDNSKNTLYLQMNSLRAEDTAVYYCASEPLSNHCWWGQGTLVTVSS | 18 |
| MN19 | Heavy chain | EVQLVESGGGLVQPGGSLRLSCAASGFTFTTYYMGWVRQAPGKGPEVVSLISGDGSNTWYDDSVKGRFTISRDNSKNTLYLQMNSLRAEDTAVYYCARYDCLSPASYDYWGQGTLVTVSS | 19 |
| MN20 | Heavy chain | EVQLVESGGGLVQPGGSLRLSCAASGFTFSSYAMGWVRQAPGKGPEVVSLISGSGGSTWYDDSVKGRFTISRDNSKNTLYLQMNSLRAEDTAVYYCASTGTGNMRWFTWGQGTLVTVSS | 20 |

TABLE 2

| Clone | Variable domain | VH-CDR1 | VH-CDR2 | VH-CDR3 |
|---|---|---|---|---|
| MN1 | Heavy chain | TAYDMG (SEQ ID NO: 21) | LISSDSGDT (SEQ ID NO: 22) | LGAYSTTYDY (SEQ ID NO: 23) |
| MN2 | Heavy chain | TNYDMG (SEQ ID NO: 24) | LISGGSET (SEQ ID NO: 25) | METSHTNDTDY (SEQ ID NO: 26) |
| MN3 | Heavy chain | SSYAMG (SEQ ID NO: 27) | LISGSGGST (SEQ ID NO: 28) | FRKTTQETNT (SEQ ID NO: 29) |
| MN4 | Heavy chain | SSYAMG (SEQ ID NO: 27) | LISGSGGST (SEQ ID NO: 28) | MRLPYSNEASHT (SEQ ID NO: 30) |
| MN5 | Heavy chain | SSYAMG (SEQ ID NO: 27) | LISGSGGST (SEQ ID NO: 28) | REDNMTT (SEQ ID NO: 31) |
| MN6 | Heavy chain | SSYAMG (SEQ ID NO: 27) | LISGSGGST (SEQ ID NO: 28) | LRSPSQHHGR (SEQ ID NO: 32) |
| MN7 | Heavy chain | SSYAMG (SEQ ID NO: 27) | LISGSGGST (SEQ ID NO: 28) | PEDMYQT (SEQ ID NO: 33) |
| MN8 | Heavy chain | SSYAMG (SEQ ID NO: 27) | LISGSGGST (SEQ ID NO: 28) | PEDAPSYSR (SEQ ID NO: 34) |
| MN9 | Heavy chain | SSYAMG (SEQ ID NO: 27) | LISGSGGST (SEQ ID NO: 28) | PEDTYQP (SEQ ID NO: 35) |
| MN10 | Heavy chain | SSYAMG (SEQ ID NO: 27) | LISGSGGST (SEQ ID NO: 28) | YLRPRIEAHNT (SEQ ID NO: 36) |
| MN11 | Heavy chain | SSYAMG (SEQ ID NO: 27) | LISGSGGST (SEQ ID NO: 28) | YQSPGADAHNR (SEQ ID NO: 37) |
| MN12 | Heavy chain | SSYAMG (SEQ ID NO: 27) | LISGSGGST (SEQ ID NO: 28) | FRFSTIQMNQ (SEQ ID NO: 38) |
| MN13 | Heavy chain | SSYAMG (SEQ ID NO: 27) | LISGSGGST (SEQ ID NO: 28) | YPHDGNP (SEQ ID NO: 39) |

TABLE 2-continued

| Clone | Variable domain | VH-CDR1 | VH-CDR2 | VH-CDR3 |
|---|---|---|---|---|
| MN14 | Heavy chain | SSYAMG (SEQ ID NO: 27) | LISGSGGST (SEQ ID NO: 28) | FRPPECQAPG (SEQ ID NO: 40) |
| MN15 | Heavy chain | SSYAMG (SEQ ID NO: 27) | LISGSGGST (SEQ ID NO: 28) | FRRYQSETNT (SEQ ID NO: 41) |
| MN16 | Heavy chain | SSYAMG (SEQ ID NO: 27) | LISGSGGST (SEQ ID NO: 28) | FSTPSSSRHN (SEQ ID NO: 42) |
| MN17 | Heavy chain | SSYAMG (SEQ ID NO: 27) | LISGSGGST (SEQ ID NO: 28) | ALAPFKTTLK (SEQ ID NO: 43) |
| MN18 | Heavy chain | SSYAMG (SEQ ID NO: 27) | LISGSGGST (SEQ ID NO: 28) | EPLSNHCW (SEQ ID NO: 44) |
| MN19 | Heavy chain | TTYYMG (SEQ ID NO: 45) | LISGDGSNT (SEQ ID NO: 46) | YDCLSPASYDY (SEQ ID NO: 47) |
| MN20 | Heavy chain | SSYAMG (SEQ ID NO: 27) | LISGSGGST (SEQ ID NO: 28) | TGTGNMRWFT (SEQ ID NO: 48) |

(3) Measurement of Antigen Binding Capacity of Anti-BCMA Antibody

Among the selected 20 clones, Clones MN1, MN5, MN7, and MN8 which were expected to have excellent binding capacity to BCMA-expressing tumor cell lines were purified. Quantitative binding capacity (affinity) of Clones MN1, MN5, MN7, and MN8 to recombinant human BCMA was measured using the OCTET system (Pall Corporation). BCMA (Cat. No. 193-BC, R&D Systems) purified from HEK293 cells was fixed to Biosensor (Pall Corporation). Then, the MN1, MN5, MN7, or MN8 antibody diluted sequentially in Kinetic bfr (Pall Corporation) was allowed to associate in a concentration range of 0.078 nM to 5 nM for 120 seconds, and was allowed to dissociate by performing flowing at a flow rate of 30 µl/min for 1,800 seconds. Dissociation of the BCMA-bound antibody was induced by flowing 10 mM glycine-HCl pH 1.5 at a flow rate of 30 µl/min for 30 seconds (Table 3). The binding affinity was obtained as the kinetic parameters (Kon and Koff) and the equilibrium dissociation constant (KD) using the Octet system data analysis software (Table 4).

TABLE 3

| | |
|---|---|
| Octet | ForteBio Octet system |
| Chip | Anti-Fc Biosensor |
| Running buffer | Kinetic buffer |
| Flow rate | 30 µl/min |
| Association/dissociation time | 120 seconds/600 seconds |
| IgG concentration | 0.078 to 5 nM, ½ serial dilution |
| Regeneration | 10 mM Glycine-HCl pH 1.5, 30 seconds |

TABLE 4

| Clone | $K_{on}$ | $K_{off}$ | $K_D$ |
|---|---|---|---|
| MN1 | $2.51 \times 10^5$ | $1.75 \times 10^{-4}$ | $7.00 \times 10^{-10}$ |
| MN5 | $1.54 \times 10^5$ | $3.43 \times 10^{-4}$ | $2.22 \times 10^{-9}$ |
| MN7 | $1.44 \times 10^5$ | $3.21 \times 10^{-4}$ | $2.23 \times 10^{-9}$ |
| MN8 | $2.55 \times 10^5$ | $2.98 \times 10^{-4}$ | $1.17 \times 10^{-9}$ |

Example 2: Evaluation of Binding Capacity of Anti-BCMA Antibody to BCMA-Expressing Cancer Cells To evaluate whether anti-BCMA antibodies derived from the synthetic library selectively bind to BCMA-expressing cells, an expression level of BCMA in cancer cell lines was measured and antibody binding was identified by FACS testing.

(1) Identification of Expression Level of BCMA in Tumor Cell Line

Expression of cell surface BCMA was identified by FACS testing in two multiple myeloma cell lines (MM1S, H929) and one breast cancer cell line (MB231, negative control). Each of the multiple myeloma cell lines and the breast cancer cell line in culture was placed in a 50 ml tube and centrifuged at 1,000 rpm for 5 minutes at room temperature. Then, the culture solution was discarded and washing with PBS was performed once. The residue was suspended in FACS buffer, and then transferred to a round bottom tube. Centrifugation was performed at 2,000 rpm for 3 minutes at room temperature. The supernatant was discarded and loosening was performed with FACS buffer so as to obtain $1 \times 10^6$ cells/100 Anti-BCMA antibody (Abcam) was used as a FACS assay antibody against BCMA at 4° C. After 30 minutes, washing with FACS buffer was performed twice. PE-conjugated antibodies were added thereto in an amount of 0.5 µl per sample, and allowed for binding at 4° C. for 30 minutes. The cells were collected by centrifugation at 1,500 rpm for 5 minutes. Then, 300 µl of fixation buffer was added thereto, and the cells were resuspended. Then, measurement was performed by FACS fortessa. The results are illustrated in FIG. 2.

As illustrated in FIG. 2, BCMA expression was identified in the two multiple myeloma cell lines (MM1S, H929) and higher BCMA expression was identified in H929.

(2) Selection of Anti-BCMA Antibody Having Binding Capacity to BCMA-Expressing Tumor Cell Line Among the 20 antibodies selected through the phage display, FACS testing was conducted to select antibodies having binding capacity to the BMCA expressing multiple myeloma cell line H929. As a negative control, the breast cancer cell line MB231 that does not express BCMA was used.

For analysis of selective binding, a total of 20 antibody E. coli soups were used for FACS screening, and a FITC-conjugated anti-BCMA antibody (LSBio, LS-C18662) was used as a positive control. FACS testing was performed by treatment with the same amount of E. coli soup in which the VH domain had been expressed.

Multiple myeloma cells in culture were placed in a 50 ml tube, and centrifuged at 1,000 rpm for 5 minutes at room temperature. Then, the culture solution was discarded and washing with PBS was performed once. The residue was suspended in FACS buffer and then transferred to a round bottom tube. Centrifugation was performed at 2,000 rpm for 3 minutes at room temperature. The supernatant was discarded and loosening was performed with FACS buffer so as to obtain 1×10⁶ cells/100 μl, and then an E. coli supernatant containing the candidate antibody was added thereto at 4° C.

As a negative control, FACS buffer containing no candidate antibody was added. After 30 minutes, washing with FACS buffer was performed twice. 1 μl of FITC-linked mouse-derived anti-HA probe IgG antibody (Santa Cruze, sc7392-FITC) was added per sample, and allowed for binding at 4° C. for 30 minutes. The cells were collected by centrifugation at 2,000 rpm for 3 minutes, and then 200 μl of fixation buffer was added thereto. The cells were resuspended and then measured by FACS Calibur™. The results are illustrated in FIG. 3. Referring to the graph in FIG. 3, relative binding capacity in the breast cancer cell line MB231 and the multiple myeloma cell line H929 is indicated as OD values.

Through FACS analysis, it was found that among the 20 candidate antibodies, four antibodies (MN1, MN5, MN7, MN8) show binding capacity to H929 cell line (FIG. 3). It was identified that when the binding capacity is converted into an MFI value relative to their comparative antibody, Clones MN1, MN5, MN7, and MN8 exhibited the highest binding affinity to BCMA in this order, and in particular, MN1 was shown to exhibit the best binding affinity.

(3) Analysis of Selective Binding of Anti-BCMA Antibody to BCMA-Expressing Tumor Cell Line The four antibodies, MN1, MN5, MN7, and MN8, which are shown to have binding capacity to the multiple myeloma cell lines H929 and MM1S which express BMCA, were purified, and it was identified through FACS testing whether the anti-BCMA antibodies selectively bind to the multiple myeloma cell lines. As a negative control, the breast cancer cell line MB231 that does not express BCMA was used.

The antibody clones used for FACS screening for analysis of selective binding are shown in Table 5. FACS testing was conducted in two forms, that is, VH domain alone (FIG. 4) and VH-Fc protein (FIG. 5). Here, as the Fc domain, a human IgG1 Fc domain was used.

TABLE 5

| Source | Number | Clones |
|---|---|---|
| Synthetic library | 4 | MN1, MN5, MN7, MN8 |

Multiple myeloma cells in culture were placed in a 50 ml tube and centrifuged at 1,000 rpm for 5 minutes at room temperature. Then, the culture solution was discarded and washing with PBS was performed once. The resultant was suspended in FACS buffer and then transferred to a round bottom tube. Centrifugation was performed at 2,000 rpm for 3 minutes at room temperature. The supernatant was discarded and loosening was performed with FACS buffer so as to obtain 1×10⁶ cells/100 μl. Then, 1 uM of the purified candidate antibody was added thereto at 4° C.

As a control, FACS buffer containing no candidate antibody was added. After 30 minutes, washing with FACS buffer was performed twice. 1 μl of FITC-linked mouse-derived anti-HA probe IgG antibody (Santa Cruze, sc7392-FITC) was added per sample, and allowed for binding at 4° C. for 30 minutes. The cells were collected by centrifugation at 2,000 rpm for 3 minutes, and then 200 μl of fixation buffer was added thereto. The cells were resuspended and measured by FACS Calibur™. The results are illustrated in FIGS. 4 and 5.

The graphs in (A) of FIGS. 4 and 5 show relative binding capacity of the purified antibodies, specifically, binding capacity of MN1, MN5, MN7, MN8, and negative control antibodies in order from top to bottom, in the breast cancer cell line MB231, and the multiple myeloma cell lines MM1S and H929. The results in (B) of FIGS. 4 and 5 numerically indicate the values in the graphs in (A).

Referring to FIGS. 4 and 5, it can be seen that all four antibodies showed binding capacity to MM1S and H929 cell lines which express BCMA. It was identified that when the binding capacity is converted into an 1VIFI value relative to their comparative antibody, Clones MN1, MN5, MN7, and MN8 exhibited the highest binding affinity to BCMA in this order, and in particular, MN1 was shown to exhibit the best binding affinity.

Although the embodiments have been described by a limited number of examples and the drawings as described above, it will be apparent to those skilled in the art that various changes and modifications may be made without departing from the spirit and scope of the invention. For example, it is possible to achieve desired results even in a case where the techniques as described are performed in a different order than the described method, and/or the components as described are assembled or combined in a different form than the described method, or replaced or substituted by other components or equivalents.

Therefore, other implementations, other embodiments, and equivalents of the appended claims fall within the scope of the appended claims.

The invention claimed is:

1. An antibody or a fragment thereof which specifically binds to B-cell maturation antigen (BCMA), said antibody or fragment thereof comprising:
   a heavy chain variable domain (VH domain) comprising the amino acid sequence of any one of SEQ ID NOs: 1, 3 to 18, and 20.

2. The antibody or a fragment thereof of claim 1, which comprises a heavy chain variable domain comprising the amino acid sequence of SEQ ID NO: 1, 5, 7, or 8.

3. An antibody or a fragment thereof, which specifically binds to B-cell maturation antigen (BCMA), comprising:
   VH-CDR1 comprising the amino acid sequence of SEQ ID NO: 21 or 27;
   VH-CDR2 comprising the amino acid sequence of SEQ ID NO: 22 or 28; and
   VH-CDR3 comprising the amino acid sequence of SEQ ID NO: 23, 29, 30, 31, 32, 33, 34, 35, 36, 37, 38, 39, 40, 41, 42, 43, 44, or 48.

4. The antibody or a fragment thereof of claim 3, wherein the VH-CDR3 comprising the amino acid sequence of SEQ ID NO: 23, 31, 33, or 34.

5. The antibody or a fragment thereof of claim 1, wherein the antibody is a humanized antibody.

6. The antibody or a fragment thereof of claim 1, wherein the fragment of the antibody is a single-domain antibody (sdAb).

7. A pharmaceutical composition, comprising the antibody or a fragment thereof of claim 1.

8. A method for treating cancer in a subject in need thereof, comprising administering the pharmaceutical composition of claim 7 to the subject, wherein the subject has cancer cells expressing BCMA.

9. The method of claim 8, wherein the cancer is multiple myeloma (MM).

10. The antibody or a fragment thereof of claim 3, wherein the antibody is a humanized antibody.

11. The antibody or a fragment thereof of claim 3, wherein the fragment of the antibody is a single-domain antibody (sdAb).

12. A pharmaceutical composition, comprising the antibody or a fragment thereof of claim 3.

13. A method for treating cancer in a subject in need thereof, comprising administering the pharmaceutical composition of claim 12 to the subject, wherein the subject has cancer cells expressing BCMA.

14. The method of claim 13, wherein the cancer is multiple myeloma (MM).

15. The method of claim 8, wherein the cancer is solid cancer expressing BCMA.

16. The method of claim 8, wherein the cancer is blood cancer expressing BCMA.

17. The method of claim 13, wherein the cancer is solid cancer expressing BCMA.

18. The method of claim 13, wherein the cancer is blood cancer expressing BCMA.

19. An antibody or a fragment thereof, which specifically binds to B-cell maturation antigen (BCMA), comprising:
   VH-CDR1 comprising the amino acid sequence of SEQ ID NO: 21, VH-CDR2 comprising the amino acid sequence of SEQ ID NO: 22, and VH-CDR3 comprising the amino acid sequence of SEQ ID NO: 23, or
   VH-CDR1 comprising the amino acid sequence of SEQ ID NO: 27, VH-CDR2 comprising the amino acid sequence of SEQ ID NO: 28, and VH-CDR3 comprising the amino acid sequence of SEQ ID NO: 29, 30, 31, 32, 33, 34, 35, 36, 37, 38, 39, 40, 41, 42, 43, 44, or 48.

20. A conjugate comprising the antibody or a fragment thereof of claim 1 and a drug or an Fc domain conjugated thereto, wherein the drug is maytansinoid, auristatin, dolastatin, trichothecene, CC1065 (NSC 298223), calicheamicin, taxane, anthracycline, methotrexate, adriamycin, vindesine, vinca alkaloids, doxorubicin, melphalan, mitomycin C, chlorambucil, daunorubicin, daunomycin, etoposide, teniposide, carminomycin, aminopterin, dactinomycin, mitomycins, bleomycins, esperamicins, 5-fluorouracil, cis-platinum, nuclease, antibiotic, toxin, cisplatin, CPT-11, paclitaxel, docetaxel, miRNA, siRNA, or shRNA.

21. A method for treating cancer in a subject in need thereof, comprising administering the conjugate of claim 20 or a pharmaceutical composition comprising the conjugate to the subject, wherein the subject has cancer cells expressing BCMA.

22. A chimeric antigen receptor (CAR) comprising an extracellular domain comprising an antibody moiety, a transmembrane domain, and an intracellular signaling domain, wherein the antibody moiety comprises the antibody or a fragment thereof of claim 1.

23. An effector cell expressing the CAR of claim 22, wherein the effector cell is a T cell or a natural killer (NK) cell.

24. A chimeric antigen receptor (CAR) comprising an extracellular domain comprising an antibody moiety, a transmembrane domain, and an intracellular signaling domain, wherein the antibody moiety comprises the antibody or a fragment thereof of claim 3.

25. An effector cell expressing the CAR of claim 24, wherein the effector cell is a T cell or a natural killer (NK) cell.

26. A bispecific antibody or a fragment thereof, comprising a first antibody or a fragment thereof, said first antibody or a fragment thereof being the antibody or a fragment thereof of claim 1 and a second antibody or an antigen binding fragment thereof selected from the group consisting of an antibody or a fragment therefor specifically binding to TCR/CD3, CD16 (FcγRIIIa), CD44, CD56, CD69, CD64 (FcγRI), CD89, and CD11b/CD18 (CR3).

27. A bispecific antibody or a fragment thereof, comprising a first antibody or a fragment thereof, said first antibody or a fragment thereof being the antibody or a fragment thereof of claim 3 and a second antibody or an antigen binding fragment thereof selected from the group consisting of an antibody or a fragment therefor specifically binding to TCR/CD3, CD16 (FcγRIIIa), CD44, CD56, CD69, CD64 (FcγRI), CD89, and CD11b/CD18 (CR3).

* * * * *

SEQUENCE LISTING

<160> NUMBER OF SEQ ID NOS: 48

<210> SEQ ID NO 1
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ala Tyr
            20                  25                  30

Asp Met Gly Trp Val Arg Gln Ala Pro Gly Lys Gly Pro Glu Trp Val
        35                  40                  45

Ser Leu Ile Ser Ser Asp Ser Gly Asp Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Tyr Ser Thr Thr Tyr Asp Tyr Trp Gly Gln Gly
            100                 105                 110

Thr Leu Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Asp Met Gly Trp Val Arg Gln Ala Pro Gly Lys Gly Pro Glu Trp Val
        35                  40                  45

Ser Leu Ile Ser Gly Gly Ser Glu Thr Trp Tyr Asp Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Met Glu Thr Ser His Thr Asn Asp Thr Asp Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

```
Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Phe Arg Lys Thr Thr Gln Gly Thr Asn Thr Trp Gly Gln Gly
                100                 105                 110

Thr Leu Val Thr Val Ser Ser
            115

<210> SEQ ID NO 4
<211> LENGTH: 121
<212> TYPE: PRT
<213> ORGANISM: Artificial Sequence
<220> FEATURE:
<223> OTHER INFORMATION: VH domain of anti-BCMA antibody

<400> SEQUENCE: 4

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Gly Trp Val Arg Gln Ala Pro Gly Lys Gly Pro Glu Val Val
             35                  40                  45

Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Met Arg Leu Pro Tyr Ser Asn Glu Ala Ser His Thr Trp Gly
                100                 105                 110

Gln Gly Thr Leu Val Thr Val Ser Ser
        115                 120

<210> SEQ ID NO 5
<211> LENGTH: 116
<212> TYPE: PRT
<213> ORGANISM: Artificial Sequence
<220> FEATURE:
<223> OTHER INFORMATION: VH domain of anti-BCMA antibody

<400> SEQUENCE: 5

Glu Val Gln Leu Val Glu Ser Gly Gly Gly Leu Val Gln Pro Gly Gly
  1               5                  10                  15

Ser Leu Arg Leu Ser Cys Ala Ser Gly Phe Thr Phe Ser Ser Tyr
                 20                  25                  30

Ala Met Gly Trp Val Arg Gln Ala Pro Gly Lys Gly Pro Glu Val Val
             35                  40                  45

Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Ser Arg Glu Asp Asn Met Thr Thr Trp Gly Gln Gly Thr Leu Val
            100                 105                 110

Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Arg Ser Pro Ser Gln His His Gly Arg Trp Gly Gln Gly
            100                 105                 110

Thr Leu Val Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: VH domain of anti-BCMA antibody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Glu Asp Met Tyr Gln Thr Trp Gly Gln Gly Thr Leu Val
            100                 105                 110

Thr Val Ser Ser
        115

<210> SEQ ID NO 8
<211> LENGTH: 118
<212> TYPE: PRT
<213> ORGANISM: Artificial Sequence
```

```
<220> FEATURE:
<223> OTHER INFORMATION: VH domain of anti-BCMA antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Glu Asp Ala Pro Ser Tyr Ser Arg Trp Gly Gln Gly Thr
            100                 105                 110

Leu Val Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: VH domain of anti-BCMA antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Glu Asp Thr Tyr Gln Pro Trp Gly Gln Gly Thr Leu Val
            100                 105                 110

Thr Val Ser Ser
        115

<210> SEQ ID NO 10
<211> LENGTH: 120
<212> TYPE: PRT
<213> ORGANISM: Artificial Sequence
<220> FEATURE:
<223> OTHER INFORMATION: VH domain of anti-BCMA antibody

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Tyr Leu Arg Pro Arg Thr Glu Ala His Asn Thr Trp Gly Gln
            100                 105                 110

Gly Thr Leu Val Thr Val Ser Ser
            115                 120

<210> SEQ ID NO 11
<211> LENGTH: 120
<212> TYPE: PRT
<213> ORGANISM: Artificial Sequence
<220> FEATURE:
<223> OTHER INFORMATION: VH domain of anti-BCMA antibody

<400> SEQUENCE: 11

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Tyr Gln Ser Pro Gly Ala Asp Ala His Asn Arg Trp Gly Gln
            100                 105                 110

Gly Thr Leu Val Thr Val Ser Ser
            115                 120

<210> SEQ ID NO 12
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 12

Glu Val Gln Leu Val Glu Ser Gly Gly Gly Leu Val Gln Pro Gly Gly
 1               5                  10                  15

Ser Leu Arg Leu Ser Cys Ala Ser Gly Phe Thr Phe Ser Ser Tyr
             20                  25                  30

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Phe Arg Phe Ser Thr Ile Gln Met Asn Gln Trp Gly Gln Gly
            100                 105                 110

Thr Leu Val Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: VH domain of anti-BCMA antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Tyr Pro His Asp Gly Asn Pro Trp Gly Gln Gly Thr Leu Val
            100                 105                 110

Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Phe Arg Pro Pro Glu Cys Gln Ala Pro Gly Trp Gly Gln Gly
            100                 105                 110

Thr Leu Val Thr Val Ser Ser
        115

<210> SEQ ID NO 15
<211> LENGTH: 119
<212> TYPE: PRT
<213> ORGANISM: Artificial Sequence

```
<220> FEATURE:
<223> OTHER INFORMATION: VH domain of anti-BCMA antibody

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Phe Arg Arg Tyr Gln Ser Glu Thr Asn Thr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Phe Ser Thr Pro Ser Ser Arg His Asn Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ala Leu Ala Pro Phe Lys Thr Thr Leu Lys Trp Gly Gln Gly
             100                 105                 110

Thr Leu Val Thr Val Ser Ser
            115
```

<210> SEQ ID NO 18
<211> LENGTH: 117
<212> TYPE: PRT
<213> ORGANISM: Artificial Sequence
<220> FEATURE:
<223> OTHER INFORMATION: VH domain of anti-BCMA antibody

<400> SEQUENCE: 18

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Glu Pro Leu Ser Asn His Cys Trp Trp Gly Gln Gly Thr Leu
             100                 105                 110

Val Thr Val Ser Ser
            115
```

<210> SEQ ID NO 19
<211> LENGTH: 120
<212> TYPE: PRT
<213> ORGANISM: Artificial Sequence
<220> FEATURE:
<223> OTHER INFORMATION: VH domain of anti-BCMA antibody

<400> SEQUENCE: 19

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Thr Tyr
             20                  25                  30

Tyr Met Gly Trp Val Arg Gln Ala Pro Gly Lys Gly Pro Glu Trp Val
            35                  40                  45

Ser Leu Ile Ser Gly Asp Gly Ser Asn Thr Trp Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Tyr Asp Cys Leu Ser Pro Ala Ser Tyr Asp Tyr Trp Gly Gln
            100                 105                 110

Gly Thr Leu Val Thr Val Ser Ser
        115                 120

<210> SEQ ID NO 20
<211> LENGTH: 119
<212> TYPE: PRT
<213> ORGANISM: Artificial Sequence
<220> FEATURE:
<223> OTHER INFORMATION: VH domain of anti-BCMA antibody

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Thr Gly Thr Gly Asn Met Arg Trp Phe Thr Trp Gly Gln Gly
            100                 105                 110

Thr Leu Val Thr Val Ser Ser
        115

<210> SEQ ID NO 21
<211> LENGTH: 6
<212> TYPE: PRT
<213> ORGANISM: Artificial Sequence
<220> FEATURE:
<223> OTHER INFORMATION: VH-CDR1 domain of anti-BCMA antibody

<400> SEQUENCE: 21

Thr Ala Tyr Asp Met Gly
1               5

<210> SEQ ID NO 22
<211> LENGTH: 9
<212> TYPE: PRT
<213> ORGANISM: Artificial Sequence
<220> FEATURE:
<223> OTHER INFORMATION: VH-CDR2 domain of anti-BCMA antibody

<400> SEQUENCE: 22

Leu Ile Ser Ser Asp Ser Gly Asp Thr
1               5

<210> SEQ ID NO 23
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 23

Leu Gly Ala Tyr Ser Thr Thr Tyr Asp Tyr
1               5                   10

```
<210> SEQ ID NO 24
<211> LENGTH: 6
<212> TYPE: PRT
<213> ORGANISM: Artificial Sequence
<220> FEATURE:
<223> OTHER INFORMATION: VH-CDR1 domain of anti-BCMA antibody

<400> SEQUENCE: 24

Thr Asn Tyr Asp Met Gly
1               5

<210> SEQ ID NO 25
<211> LENGTH: 8
<212> TYPE: PRT
<213> ORGANISM: Artificial Sequence
<220> FEATURE:
<223> OTHER INFORMATION: VH-CDR2 domain of anti-BCMA antibody

<400> SEQUENCE: 25

Leu Ile Ser Gly Gly Ser Glu Thr
1               5

<210> SEQ ID NO 26
<211> LENGTH: 11
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 26

Met Glu Thr Ser His Thr Asn Asp Thr Asp Tyr
1               5                   10

<210> SEQ ID NO 27
<211> LENGTH: 6
<212> TYPE: PRT
<213> ORGANISM: Artificial Sequence
<220> FEATURE:
<223> OTHER INFORMATION: VH-CDR1 domain of anti-BCMA antibody

<400> SEQUENCE: 27

Ser Ser Tyr Ala Met Gly
1               5

<210> SEQ ID NO 28
<211> LENGTH: 9
<212> TYPE: PRT
<213> ORGANISM: Artificial Sequence
<220> FEATURE:
<223> OTHER INFORMATION: VH-CDR2 domain of anti-BCMA antibody

<400> SEQUENCE: 28

Leu Ile Ser Gly Ser Gly Gly Ser Thr
1               5

<210> SEQ ID NO 29
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 29

Phe Arg Lys Thr Thr Gln Glu Thr Asn Thr
1               5                   10
```

```
<210> SEQ ID NO 30
<211> LENGTH: 12
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 30

Met Arg Leu Pro Tyr Ser Asn Glu Ala Ser His Thr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 31

Arg Glu Asp Asn Met Thr Thr
1               5

<210> SEQ ID NO 32
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 32

Leu Arg Ser Pro Ser Gln His His Gly Arg
1               5                   10

<210> SEQ ID NO 33
<211> LENGTH: 7
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 33

Pro Glu Asp Met Tyr Gln Thr
1               5

<210> SEQ ID NO 34
<211> LENGTH: 9
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 34

Pro Glu Asp Ala Pro Ser Tyr Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 35

Pro Glu Asp Thr Tyr Gln Pro
1               5
```

```
<210> SEQ ID NO 36
<211> LENGTH: 11
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 36

Tyr Leu Arg Pro Arg Thr Glu Ala His Asn Thr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 37

Tyr Gln Ser Pro Gly Ala Asp Ala His Asn Arg
1               5                   10

<210> SEQ ID NO 38
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 38

Phe Arg Phe Ser Thr Ile Gln Met Asn Gln
1               5                   10

<210> SEQ ID NO 39
<211> LENGTH: 7
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 39

Tyr Pro His Asp Gly Asn Pro
1               5

<210> SEQ ID NO 40
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 40

Phe Arg Pro Pro Glu Cys Gln Ala Pro Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 41

Phe Arg Arg Tyr Gln Ser Glu Thr Asn Thr
1               5                   10
```

<210> SEQ ID NO 42
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 42

Phe Ser Thr Pro Ser Ser Ser Arg His Asn
1               5                   10

<210> SEQ ID NO 43
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 43

Ala Leu Ala Pro Phe Lys Thr Thr Leu Lys
1               5                   10

<210> SEQ ID NO 44
<211> LENGTH: 8
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 44

Glu Pro Leu Ser Asn His Cys Trp
1               5

<210> SEQ ID NO 45
<211> LENGTH: 6
<212> TYPE: PRT
<213> ORGANISM: Artificial Sequence
<220> FEATURE:
<223> OTHER INFORMATION: VH-CDR1 domain of anti-BCMA antibody

<400> SEQUENCE: 45

Thr Thr Tyr Tyr Met Gly
1               5

<210> SEQ ID NO 46
<211> LENGTH: 9
<212> TYPE: PRT
<213> ORGANISM: Artificial Sequence
<220> FEATURE:
<223> OTHER INFORMATION: VH-CDR2 domain of anti-BCMA antibody

<400> SEQUENCE: 46

Leu Ile Ser Gly Asp Gly Ser Asn Thr
1               5

<210> SEQ ID NO 47
<211> LENGTH: 11
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 47

Tyr Asp Cys Leu Ser Pro Ala Ser Tyr Asp Tyr
1               5                   10

```
<210> SEQ ID NO 48
<211> LENGTH: 10
<212> TYPE: PRT
<213> ORGANISM: Artificial Sequence
<220> FEATURE:
<223> OTHER INFORMATION: VH-CDR3 domain of anti-BCMA antibody

<400> SEQUENCE: 48

Thr Gly Thr Gly Asn Met Arg Trp Phe Thr
1               5                   10
```